(12) United States Patent
Stochniol et al.

(10) Patent No.: US 9,856,184 B2
(45) Date of Patent: Jan. 2, 2018

(54) REGENERATION OF A HETEROGENEOUS CATALYST IN ETHENE OLIGOMERIZATION

(71) Applicant: EVONIK DEGUSSA GMBH, Essen (DE)

(72) Inventors: Guido Stochniol, Haltern am See (DE); Stephan Peitz, Oer-Erkenschwick (DE); Dietrich Maschmeyer, Recklinghausen (DE); Helene Reeker, Dortmund (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/056,147

(22) Filed: Feb. 29, 2016

(65) Prior Publication Data
US 2016/0257630 A1  Sep. 8, 2016

(30) Foreign Application Priority Data

Mar. 3, 2015 (EP) .................... 15157358

(51) Int. Cl.
| | | |
|---|---|---|
| B01J 38/56 | (2006.01) | |
| C07C 2/10 | (2006.01) | |
| C07C 2/12 | (2006.01) | |
| C07C 2/24 | (2006.01) | |
| C07C 41/06 | (2006.01) | |

(52) U.S. Cl.
CPC ............ *C07C 2/24* (2013.01); *B01J 38/56* (2013.01); *C07C 2/10* (2013.01); *C07C 2/12* (2013.01); *C07C 41/06* (2013.01); *C07C 2521/12* (2013.01); *C07C 2523/755* (2013.01); *Y02P 20/52* (2015.11); *Y02P 20/584* (2015.11)

(58) Field of Classification Search
CPC ... B01J 38/56; C07C 2/10; C07C 2/12; C07C 2/24; C07C 41/06
See application file for complete search history.

(56) References Cited

U.S. PATENT DOCUMENTS

| | | | |
|---|---|---|---|
| 2,581,228 A | 1/1952 | Bailey et al. | |
| 3,459,826 A * | 8/1969 | Barnett ............... | C07C 2/34 502/152 |
| 4,213,001 A * | 7/1980 | Madgavkar ........ | C07C 2/20 585/510 |
| 4,288,648 A | 9/1981 | Beach et al. | |
| 4,482,640 A * | 11/1984 | Knudsen ............. | B01J 31/04 502/155 |
| 4,567,307 A * | 1/1986 | Jones ................... | C07C 2/84 585/330 |
| 4,576,926 A * | 3/1986 | Wang .................. | B01J 37/024 502/325 |
| 5,051,386 A * | 9/1991 | Ward ................... | B01J 27/16 502/214 |
| 6,015,932 A | 1/2000 | Frey | |
| 7,294,741 B2 | 11/2007 | Bub et al. | |
| 7,939,597 B2 | 5/2011 | Bub et al. | |
| 8,198,481 B2 | 6/2012 | Kuppinger et al. | |
| 8,258,249 B2 | 9/2012 | Bub et al. | |
| 8,293,941 B2 | 10/2012 | Kuppinger et al. | |
| 8,481,784 B2 | 7/2013 | Kuppinger et al. | |
| 8,524,945 B2 | 9/2013 | Stochniol et al. | |
| 8,895,683 B2 | 11/2014 | Kuppinger et al. | |
| 9,255,229 B2 | 2/2016 | Borremans et al. | |
| 2003/0171204 A1 | 9/2003 | Winder et al. | |
| 2004/0124140 A1 | 7/2004 | Sawyer et al. | |
| 2004/0242404 A1 | 12/2004 | Hwang et al. | |
| 2011/0000697 A1 | 1/2011 | Tsurimoto et al. | |
| 2012/0149549 A1 | 6/2012 | Boeing et al. | |

FOREIGN PATENT DOCUMENTS

| | | |
|---|---|---|
| DE | 102005026213 A1 | 12/2006 |
| DE | 102009027408 A1 | 1/2011 |
| EP | 0136026 B1 | 3/1989 |
| GB | 1196889 A | 7/1970 |
| JP | 2006512198 | 4/2006 |
| JP | 2013537566 | 10/2013 |
| WO | 2004080591 A1 | 9/2004 |
| WO | 2006022803 A1 | 3/2006 |
| WO | 2010110801 A1 | 9/2010 |
| WO | 2011112184 A1 | 9/2011 |
| WO | 2011136765 A1 | 11/2011 |
| WO | 2014082689 A1 | 6/2014 |

OTHER PUBLICATIONS

Stochniol et al., U.S. Appl. No. 15/000,807, filed Jan. 19, 2016.
Stochniol et al., U.S. Appl. No. 15/000,837, filed Jan. 19, 2016.

* cited by examiner

*Primary Examiner* — Pancham Bakshi
*Assistant Examiner* — Mark Luderer
(74) *Attorney, Agent, or Firm* — Philip P. McCann; Smith Moore Leatherwood LLP (57) ABSTRACT

The invention relates to the in situ regeneration of heterogeneous oligomerization catalysts which are used in the liquid phase oligomerization of ethene.

20 Claims, 7 Drawing Sheets

REGENERATION OF A HETEROGENEOUS CATALYST IN ETHENE OLIGOMERIZATION

The present application hereby claims priority to European Application No. EP 15 157 358.1 filed Mar. 5, 2015, which is incorporated herein by reference in its entirety.

FIELD

The invention is concerned with the regeneration of heterogeneous catalysts which are used in the liquid phase oligomerization of ethene.

BACKGROUND

Ethene (synonym: ethylene) is the simplest olefin (alkene). Its empirical formula is $C_2H_4$; it therefore has two carbon atoms and is also referred to as $C_2$ olefin. Because of its high reactivity, ethene is an important synthesis unit in the chemical industry.

By far the greatest volume of ethene is polymerized to polyethylene, one of the most widely used and ubiquitous bulk polymers, usually in the form of packaging film. Polyethylene is a chain polymer in which the ethene monomer [—$CH_2$—$CH_2$—] is repeated many times as a chain member. A polyethylene chain polymer therefore has a very large number of carbon atoms, far more than 96.

It is also possible to prepare other olefins having four, six or eight carbon atoms from ethene. This is accomplished by way of oligomerization. In ethene oligomerization, ethene reacts essentially with itself and forms olefins having more than two carbon atoms, called oligomers. For example, two ethene molecules can react to give a butene molecule, i.e. an olefin having four carbon atoms ($C_4$ olefin for short). This reaction is also referred to as dimerization; butene is the dimer of ethene. Three ethene molecules together form a hexene ($C_6$ olefin) (trimerization), and four ethene molecules form a $C_8$ olefin as oligomer (tetramerization). In parallel, two butenes formed beforehand can form an octene. This is because several reactions proceed simultaneously in parallel in the oligomerization: the primary reaction is that of ethene with itself. Secondary reactions proceed between ethene and already formed ethene oligomers or oligomers with one another.

Compared to polymerization, oligomerization gives rise to molecules having a much smaller number of carbon atoms. The limit can be set at sixteen carbon atoms. Another important feature of an oligomerization is that new olefins are formed in turn from olefins and not saturated chains.

All in all, an ethene oligomerization in the context of this invention is understood to mean the chemical reaction of ethene to form olefins having a carbon number of four to sixteen.

Ethene oligomerization is practiced in industry for preparation of $C_4$, $C_6$ and $C_8$ olefins. These serve in turn as reactants for more complex chemicals, for example higher alcohols, carboxylic acids and esters.

From a chemical engineering point of view, oligomerization processes can be divided into those which are conducted in the gas phase and those which proceed in liquid phase. In addition, heterogeneously catalyzed operations are distinguished from homogeneously catalyzed processes.

In gas phase operations, the oligomerization is conducted under conditions under which ethene is gaseous. The oligomers may then likewise be gaseous or else liquid.

In the liquid phase oligomerization, the ethene is introduced into the reactor in liquid form. Since ethene is liquid only under very high pressure, the liquid phase oligomerization of ethene is usually implemented by dissolving gaseous ethene in a liquid solvent and effecting the oligomerization in the liquid solvent. The oligomers are then also present in the solvent. The advantage of liquid phase oligomerization over gas phase oligomerization is the better exploitation of the reactor volume and better removal of the heat of reaction with the solvent (oligomerization is highly exothermic!). Overall, liquid phase oligomerization achieves a better process intensity than gas phase oligomerization.

Disadvantages of liquid phase oligomerization are the need for a solvent and the difficulty of product removal: product removal is the recovery of the oligomers from the reaction mixture which comprises, as well as the desired oligomers, also unconverted ethene, any solvent, and catalyst. If the process is homogeneously catalyzed, the catalyst is dissolved in the same phase as the reactant and the oligomerizate. If the catalyst cannot remain in the product mixture, it has to be removed accordingly. This presents additional complexity from a chemical engineering point of view.

By contrast, catalyst removal is simpler in heterogeneously catalyzed operations in which the catalyst is present in a different phase from the reactants, generally in the solid state. Both in the heterogeneously catalyzed liquid phase oligomerization and in the heterogeneously catalyzed gas phase oligomerization, the solid catalyst remains in the reactor, while the fluid product mixture is being drawn off from the reactor.

The fact that the heterogeneous catalyst remains in the reactor enables constant reuse thereof. However, this has the consequence that the catalyst loses activity with increasing service life and increasingly forms unwanted by-products. This is probably because the active sites of the catalyst become covered with deposits, such that there is no longer any contact with the ethene. These deposits are probably longer-chain by-products extending as far as low molecular weight polyethylene and/or catalyst poisons consisting of N-, O- or S-containing molecules. It is also possible for active metals in the catalyst to be oxidized in the oligomerization and hence to lose activity.

Fortunately, the deactivation of heterogeneous oligomerization catalysts is reversible: for instance, it is possible to reactivate the catalyst from time to time, as a result of which it very substantially regains its initial performance.

The prior art describes some methods of reactivating oligomerization catalysts: for instance, DE102009027408A1 describes the regeneration of a heterogeneous catalyst based on nickel oxide, silicon dioxide and aluminum dioxide. It is used preferentially in the oligomerization of $C_3$ to $C_6$ olefins. For removal of organic deposits, they are burnt off with a hot oxygenous gas stream. This is done in an oven. A disadvantage of this method is that the catalyst has to be deinstalled from the reactor and transferred into the oven for reactivation. On completion of regeneration, the catalyst has to be reinstalled in the reactor. This is associated with a comparatively large amount of manual work and causes long shutdown times of the oligomerization plant.

A simpler method in that respect is the regeneration, described in EP0136026B1, of a heterogeneous zeolite catalyst used in the mixed oligomerization of $C_2$ and $C_3$ olefins. The regeneration here is effected in situ, i.e. at the normal location of the catalyst, namely in the reactor. For the regeneration itself, the olefin stream to the catalyst is shut down and the reactor with the catalyst present therein is purged with a hot oxidizing gas. Regeneration in situ has the crucial advantage that the catalyst need not be deinstalled from the reactor and then reinstalled for regeneration. A disadvantage of this process is that the reactor has to be designed so as to have sufficient thermal stability to withstand the hot regeneration gases as well. Provided that the reactor is designed for gas phase oligomerization in any case—as is the case in EP0136026B1—the extra costs are acceptable. By contrast, making a reactor optimized for liquid phase oligomerization capable of withstanding regeneration with hot gases is associated with considerable extra costs. Furthermore, it is questionable whether all heterogeneous catalysts can be regenerated with hot gas, since the examples of EP0136026B1 are concerned solely with zeolitic catalysts. Particularly those catalysts containing nickel, chromium, iron or titanium as active metal behave completely differently in the oligomerization from the zeolites consisting solely of aluminum oxides and silicon oxides. It is therefore to be expected that such catalysts will need a different regeneration.

The regeneration of a chromium-based catalyst which is used in the liquid phase oligomerization of ethene is described in WO2014082689A1. However, this concerns a homogeneous catalyst system which is regenerating ex situ, i.e. outside the reactor.

There are also examples in the prior art of in situ regeneration of catalysts which are used in the liquid phase oligomerization of ethene (WO2011112184A1, WO2010110801A1), but these are also all homogeneous systems.

The in situ regeneration of heterogeneous catalysts which are used in the liquid phase oligomerization of ethene is not currently known to have been described to date.

SUMMARY

The problem addressed by the invention is therefore that of specifying a process for oligomerizing ethene which offers the advantages of a liquid phase process and which works with a reutilizable heterogeneous catalyst which can be regenerated with a low degree of complexity.

BRIEF DESCRIPTION OF THE FIGURES

The foregoing and other features, aspects, and advantages of the present invention will become better understood with regard to the following description, appended claims, and accompanying drawings where:

DETAILED DESCRIPTION

This problem is solved by a combined process for oligomerizing ethene over a heterogeneous catalyst and for regenerating said catalyst, having the following features:

a) the oligomerization is effected in an oligomerization operation in which ethene at least partly dissolved in a liquid solvent is contacted with the heterogeneous catalyst;

b) the regeneration is effected in a regeneration operation in which the catalyst in the absence of ethene, hydrogen and oxygen is purged with a liquid purge medium;

c) oligomerization operation and regeneration operation alternate over time, such that a time-limited oligomerization operation is followed by a time-limited regeneration operation, and the latter in turn by a time-limited oligomerization operation;

d) the heterogeneous catalyst is always at the same location, which is the reason why both oligomerization operation and regeneration operation take place at this location;

e) the location of the catalyst is supplied with thermal energy in order to impose a set temperature thereon, it being entirely possible for the actual temperature at the catalyst to deviate from the set temperature in a time- and space-limited manner;

f) the set temperature in regeneration operation is higher than the set temperature in oligomerization operation.

Since the heterogeneous catalyst is always at the same location in this process, more specifically in the reactor, the present regeneration is an in situ regeneration of the catalyst in the reactor. This has the advantage that the catalyst need not be deinstalled from the reactor.

A further essential feature of this invention is that both the oligomerization and the regeneration are effected in the liquid phase: this is because the regeneration is effected with the aid of a liquid purge medium with which the deposits are detached from the catalyst and discharged from the reactor. In order to enable the detachment, the purge medium is conducted at an elevated temperature relative to the oligomerization. This certainly means that the reactor has to have a higher thermal stability; however, the associated extra apparatus expenditure is much smaller compared to a liquid phase reactor which has to be purged with hot gas.

Finally, it is an important aspect of the invention that the regeneration is effected in the absence of ethene. Regeneration is thus not effected in the course of oligomerization operation, but at a different time in regeneration operation. According to the invention, there is thus alternation between an oligomerization operation and a regeneration operation. These two modes of operation are understood to be alternating time phases.

Furthermore, the regeneration is also effected in the absence of hydrogen or oxygen. The catalyst and its deposits are thus not oxidized. As already mentioned, ethene can be liquefied only at great pressure. In order to process it in the liquid phase at low pressure, ethene, which is intrinsically gaseous, is dissolved in a solvent which is again liquid at low pressure. In principle, it is possible to use an inert or reactive solvent. An inert solvent is understood to mean that it behaves inertly, i.e. does not react chemically, in the ethene oligomerization. A reactive solvent reacts in the oligomerization as well. Useful inert solvents are especially alkanes (paraffins) having three to ten carbon atoms per molecule. These alkanes have a higher boiling point than ethene and are consequently liquid under the oligomerization conditions desired. Because of the different boiling point, they also have good separability from ethene and the oligomers. With regard to the exact boiling point position of the solvent chosen in relation to the oligomers, reference is made to European Patent applications 15151624.2 and 15151621.8 of 19.01.2015, which were still unpublished at the filing date of the application.

In this context, it should be made clear that the cyclic alkanes having three to ten carbon atoms are also suitable as solvents and that it is of course also possible to use mixtures of two or more alkanes/cycloalkanes as solvent.

Useful reactive solvents include olefins (alkenes) having three to twelve carbon atoms or mixtures thereof. These olefins react in the oligomerization as well, and so an oligomerizate having a broader product spectrum is formed. This is called co-oligomerization. The solvent may also be a mixture of reactive and inert substances.

The same criteria apply to the selection of the purge medium. It has been found that, surprisingly, the catalyst can also be regenerated with the same substances that are suitable as solvents. A particular embodiment of the invention accordingly envisages use of the identical substance or the identical mixture as solvent and purge medium. In that case, the difference is merely that the ethene is metered into the solvent in oligomerization operation, whereas the solvent is used without ethene at higher temperature as purge medium in regeneration operation. The use of the identical solvent/purge medium has the advantage that it is merely necessary to shut down the ethene and increase the temperature at the changeover from oligomerization operation to regeneration operation. This makes the changeover of operating state very simple and automatable.

The following inert substances or mixtures thereof have been found to be particularly suitable both in the function as solvent and in the function as purge medium: propane, isobutane, pentane, cyclopentane, hexane, cyclohexane, heptane, cycloheptane.

An essential aspect of the invention is that the set temperature in regeneration operation is higher than the set temperature in oligomerization operation. In oligomerization operation, the set temperature should be between 20° C. and 130° C., and in regeneration operation between 80° C. and 150° C. Even though these intervals overlap, the proviso still applies that the set temperature chosen in regeneration operation is higher than the set temperature in oligomerization operation. It is thus not possible to combine arbitrary temperature pairs from the two ranges.

A further remark with regard to the set temperatures: as already mentioned, the oligomerization of ethene is strongly exothermic. Therefore, the oligomerization sometimes reaches temperatures above the set temperature. Consequently, the site where the oligomerization takes place (i.e. the reactor) has to be cooled to the set temperature in oligomerization operation. Nevertheless, it may be the case that temperature peaks above 130° C. occur within the reactor, and also in a locally related manner therein. The actual reaction temperature may thus quite possibly differ from the set temperature.

If an inert purge medium is being used, no perceptible reaction takes place in regeneration operation, and so heating is necessary to comply with the set temperature in regeneration operation. If, however, a reactive purge medium is used, for instance butene, it oligomerizes in the course of purging, and so the heat of reaction from the purge medium can be used to increase the set temperature in regeneration operation.

The operating conditions are preferably chosen as follows:

Oligomerization Operation:
  Pressure: $1*10^5$ Pa to $50*10^5$ Pa
  WHSV: 2 $h^{-1}$ to 50 $h^{-1}$
  Ethene content in overall solution: 1% by weight to 50% by weight Regeneration Operation:
  Pressure: $1*10^5$ Pa to $50*10^5$ Pa
  WHSV: 2 $h^{-1}$ to 50 $h^{-1}$
  Ethene content in overall solution: 0% by weight to 1% by weight The pressures should be chosen with regard to the temperatures that exist in the reactor such that the solvent or the purge medium is in the liquid state.

In oligomerization operation, the ethene content, depending on the pressure and temperature, is preferably chosen such that the ethene is dissolved completely in the liquid phase. Alternatively, it is also possible to meter in more ethene, such that some of the ethene is dissolved in the liquid phase and some of the ethene is not dissolved in the solvent but forms an additional gas phase.

Preferably, the pressure and weight hourly space velocity (WHSV) chosen are identical, such that there is barely any change in load on changeover between the operating states. This is an option especially when the purge medium and solvent are identical. In that case, the only practical differences between the oligomerization operation and regeneration operation are the ethene content in the liquid and the set temperature.

Moreover, the catalyst can be reactivated more quickly than it is deactivated. Consequently, the duration of a regeneration phase can be much shorter than the duration of a production phase. In practice, the duration of the regeneration operation should be less than 20%, preferably less than 10% and most preferably less than 5% of the duration of the preceding oligomerization operation. The regeneration times can be shortened by choosing a particularly high set temperature in regeneration operation. However, the temperature should not be chosen at such a high level that the purge medium boils. It has to be ensured that liquid purging is affected.

The location of the catalyst, where the regeneration operation and oligomerization operation take place, is a reactor in the broadest sense, i.e. an apparatus which permits controlled mass and heat transfer with its environment. This is usually implemented industrially in the design of a shell and tube reactor comprising several individual reactors connected in parallel. It is also possible for a plurality of reactors to be connected in series. For the invention, it does not matter whether an individual apparatus or several apparatuses are used as reactor. What is essential is merely that the catalyst is always at the same isolated location which enables controlled mass transfer and heat transfer with the environment. However, it is quite possible for the catalyst to move within this location, for instance back and forth between a reaction zone and a regeneration zone, provided that the same mass and heat transfer with the environment is provided for both zones. It is also possible to set up two or three reactors connected in parallel at one location, one of which is in regeneration operation and another simultaneously in oligomerization operation. A third may be in standby operation. For changeover of the operating states, the function of the individual reactors is switched in a revolving manner.

The mass transfer mentioned in this context means, in regeneration operation, that the catalyst is contacted in situ with fresh purge medium, and that the latter is drawn off again from the catalyst site after contact with the catalyst. The catalyst thus comes into contact exclusively with the purge medium. More particularly, the catalyst comes into contact neither with hydrogen nor with oxygen, since neither is present in the purge medium. The catalyst is thus not oxidized in the regeneration. The catalyst can be purged continuously or in batchwise operation, preference being given to continuous regeneration.

Analogously, mass transfer in oligomerization operation means that the solid catalyst is contacted with the liquid ethene or with the ethene dissolved in the liquid solvent, and the oligomer is drawn off from the location of the catalyst while the catalyst remains in situ. The catalyst thus comes into contact only with the ethene, or with the solvent or with the oligomerizate. Oligomerization operation is likewise possible in continuous and batchwise mode, preference being given to a continuous mode of operation.

Since, in accordance with the invention, the set temperature is increased in regeneration operation, control of the heat transfer between the location of the catalyst and its environment is crucial to the success of the process. Since heat has to be removed from the location in oligomerization operation and heat has to be supplied in regeneration operation, the simplest way of controlling the temperature of location is by flow of a temperature control medium through it, and the set temperature is set by the feed temperature of the temperature control medium. According to how the set temperature of the temperature control medium is chosen, the location is supplied with positive thermal energy or negative thermal energy, i.e. heated or cooled. Depending on the thermal energy to be transferred and the heat capacity of the temperature control medium, the mass flow rate of the temperature control medium also has to be adjusted appropriately. The temperature control medium used in the simplest case is liquid water or organic oil or silicone oil, since these media have a high heat capacity. In heating operation, regeneration can also be accomplished using steam. There is no mass transfer between the temperature control medium and the reactants; only heat transfer is intended in this respect. Accordingly, the reactor should be provided with a heat exchanger which exchanges the thermal energy between reactants and temperature control media.

Alternatively or additionally, the thermal energy can be introduced into the reactor and discharged via the solvent or the purge medium. For this purpose, the solvent or the purge medium is cooled or heated prior to entry into the reactor. If a reactive dissolution or purge medium is used, the thermal energy required can also be released directly to the catalyst or taken up by chemical reaction of the solvent or the purge medium.

The heating can also be affected by electrical means, but this is unviable in terms of energy.

Viewed overall, the most effective and efficient way of controlling the temperature is via a separate temperature control medium.

A preferred variant of the process regime envisages that the purge medium is circulated in regeneration operation, and in that the purge medium circulated, away from the location of the catalyst, is purified with the aid of a separation apparatus to free it of at least some components dissolved in the purge medium. This has the advantage that the purge medium can be reutilized. The cycle mode makes sense particularly when an inert purge medium is being used, since reactive purge media are of course consumed at the catalyst. In circulation mode, particularly the alkanes or cycloalkanes having three to ten carbon atoms or mixtures thereof are suitable as purge medium.

The separation apparatus is preferably a filter or a membrane or a cold trap, or a combination of two or more of these separation apparatuses. Such separation apparatuses are generally available and suitable for removing the impurities detached from the catalyst from the purge medium again, such that the purified purge medium can be recycled again.

The cold trap is particularly preferred, since the typical impurities can be frozen out particularly efficiently. Nor is it as easily blocked as a filter or membrane. The cold trap preferably works at a temperature below 75° C. This is because the deposits can no longer be frozen out above 80° C. The lower limit for the working temperature may be set to ambient temperature, i.e. to 20° C. There is no point in cooling the cold trap any further since most deposits already precipitate out of the purge medium at about 70° C.

If a separation apparatus is provided, it is sensible to dispose it immediately beyond the reactor in the downstream direction. This prevents dissolved deposits from being introduced into downstream production units and settling therein. Furthermore, consideration should be given, even in oligomerization operation, to running the reactor output, i.e. the oligomerizate, through the separation apparatus, since it is not possible to rule out the possibility that substances already present dissolved in the oligomerizate could be deposited on the catalyst or in other plant components, especially in cycle mode. The purification of the reactor output in the course of oligomerization operation could extend the period before the next regeneration.

As already mentioned, regeneration is an option in cycle mode particularly when an inert purge medium is being used. If an at least partly reactive purge medium is being used, the purge medium should be run into another reaction after the regeneration of the catalyst. A corresponding variant of the process in which the purge medium is an alkene having three to twelve carbon atoms or a mixture of two or more such alkenes or a mixture of one or more such alkenes with at least one alkane having three to seven carbon atoms is characterized in that the purge medium in regeneration operation is drawn off from the location of the catalyst and—after purification if required—conducted to a second heterogeneous catalyst remote from the catalyst to be regenerated, and in that at least one alkene present in the purge medium is subjected to a chemical reaction over the second catalyst. The purge medium utilized is not recycled to the catalyst used in the C2 oligomerization but utilized over the second catalyst, in a second reaction. The second reaction over the second catalyst must thus be capable of converting the purge medium—as far as possible without damage to the impurities present therein. If the deposits of the regenerated catalyst dissolved in the purge medium could poison the second catalyst, the spent purge medium should be purified accordingly before entry into the second reaction. This can be effected in the same way as the purification of the purge medium conducted in the cycle process, for instance with a cold trap or another separation apparatus. If the purge medium is an olefinic purge medium, the second reaction provided may especially be a second oligomerization, an isomerization or an etherification or an oxidative dehydrogenation. If, for instance, the purge medium utilized is a mixture comprising butenes, the butenes, on completion of regeneration of the catalyst used in the $C_2$ oligomerization, can be etherified to methyl tert-butyl ether (MTBE) or oxidatively dehydrogenated to 1,3-butadiene, or oligomerized over a catalyst suitable for the oligomerization of butenes to give $C_8$ or $C_{12}$ olefins.

The alkanes, which are comparatively reactive compared to the alkenes, are virtually inert in the oligomerization. Nevertheless, there are chemical reactions in which the alkanes are not inert and which are consequently suitable for utilization of a paraffinic purge medium. These are especially pyrolytic dehydrogenations and cleavage of alkanes to alkenes (called cracking). In a separate step, it would then still be possible to add water onto the alkene to give the alcohol and then oxidize it to the carboxylic acid. Finally, the paraffinic purge medium can also be combusted and hence thermally utilized. Consequently, one variant of the process in which the purge medium is an alkane having three to seven carbon atoms or a mixture of two or more such alkanes is characterized in that the purge medium in regeneration operation is drawn off from the location of the catalyst and conducted to a second heterogeneous catalyst remote from the catalyst to be generated, and in that at least one alkane present in the purge medium is subjected to a chemical reaction over the second catalyst.

The catalyst used in the process of the invention is not in the liquid reaction phase and can consequently be referred to as heterogeneous. More specifically, the catalyst is a solid around which the liquid reaction mixture flows. Suitable and regeneratable catalysts for oligomerization of ethene are especially those catalysts which consist of at least two components, where the first component comprises at least one element which is selected from among Ni, Cr, Fe, Ti and is present in metallic and/or oxidic and/or hydridic form and the second component comprises at least one metal oxide selected from among $Al_2O_3$, $SiO_2$, $TiO_2$, $ZrO_2$. An example of a catalyst of this kind is known from U.S. Pat. No. 2,581,228.

The oligomerization is preferably run in such a way that less than 5% by weight of the ethene converted is converted to oligomers or polymers of ethene having sixteen or more than sixteen carbon atoms. This means that predominantly dimers ($C_4$ olefins), trimers ($C_6$ olefins) and tetramers ($C_8$ olefins) are formed, and additionally a few $C_{10}$ and $C_{12}$ species. Preferably, $C_4$, $C_6$ and $C_8$ olefins are formed with a total selectivity of greater than 90%. The higher oligomers of ethene or chain molecules composed of polyethylene are unwanted by-products. In this respect, the $C_2$ oligomerization differs from polyethylene production, which aims for much greater chain lengths and also does not form any olefins.

A preferred embodiment of the process envisages continuous determination of the conversion of ethene in oligomerization operation, and then changeover from oligomerization operation to regeneration operation when the conversion of ethene has dropped to a value between 95% and 100%.

The idea behind this is that regeneration is not delayed until the catalyst has already become very greatly deactivated, but the changeover to regeneration operation is already made at a relatively early stage, when the first yield losses are detectable. "Early" in this connection means when the conversion of ethene has dropped from the optimal 100% to a value between 95% and 100%. The optimal changeover to regeneration operation is at about 97% conversion. Early changeover leads overall to pulsed regeneration operation, i.e. to relatively frequent but brief regeneration phases. Long-term experiments indicate that the catalyst achieves much longer on-stream times in the case of pulsed regeneration phases, and the conversion can be run at nearly full conversion (100%) over longer periods.

Figure 1:
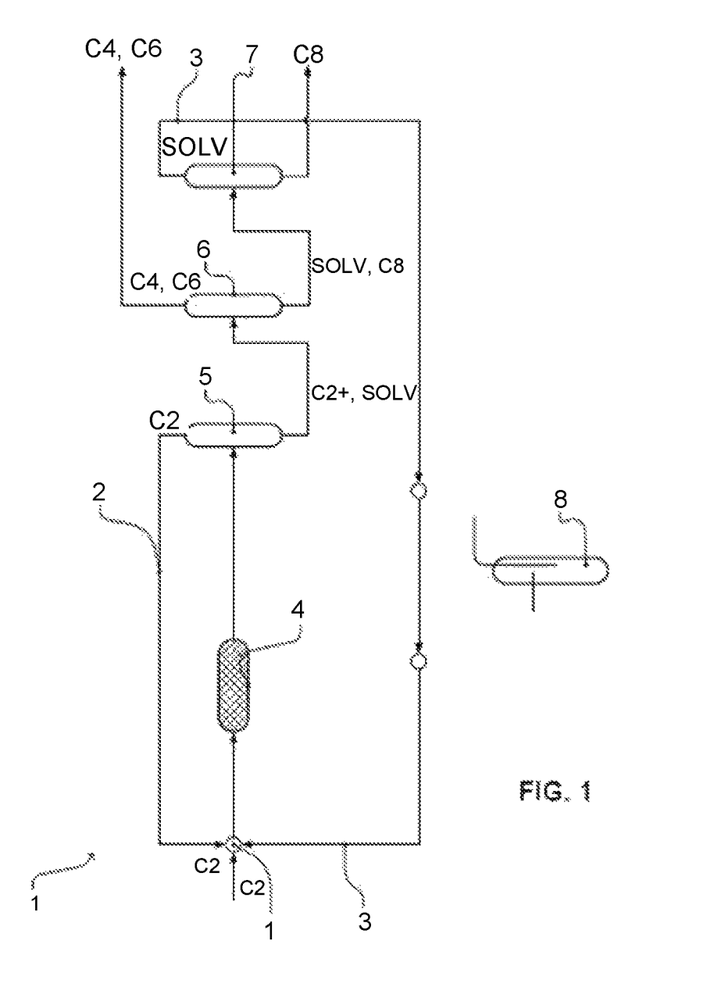
FIG. 1 shows a process flow diagram of a first embodiment I in oligomerization operation.
Figure 2:
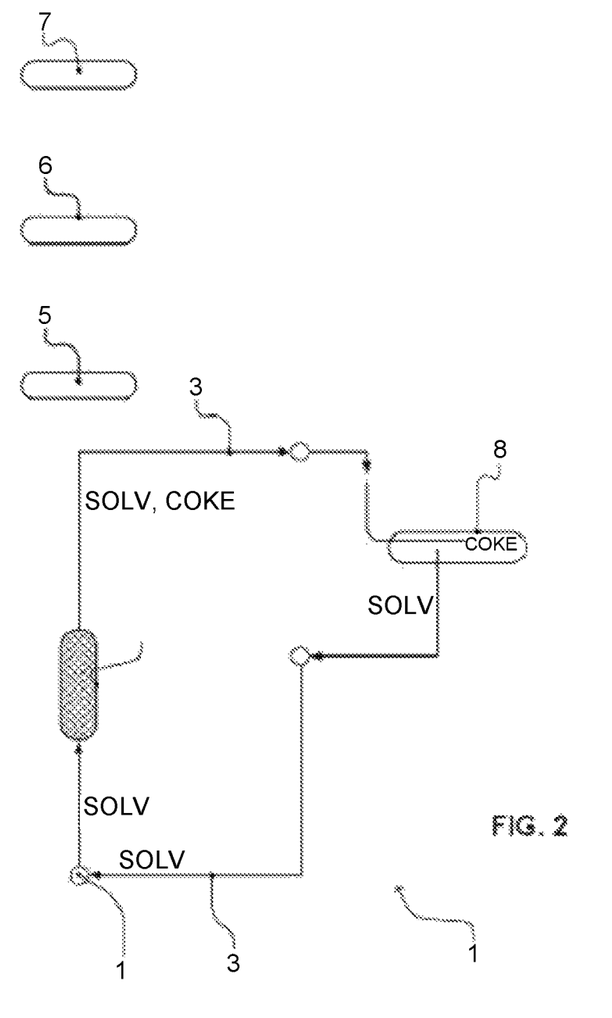
FIG. 2 shows a process flow diagram of the first embodiment I in regeneration operation.
Figure 3:
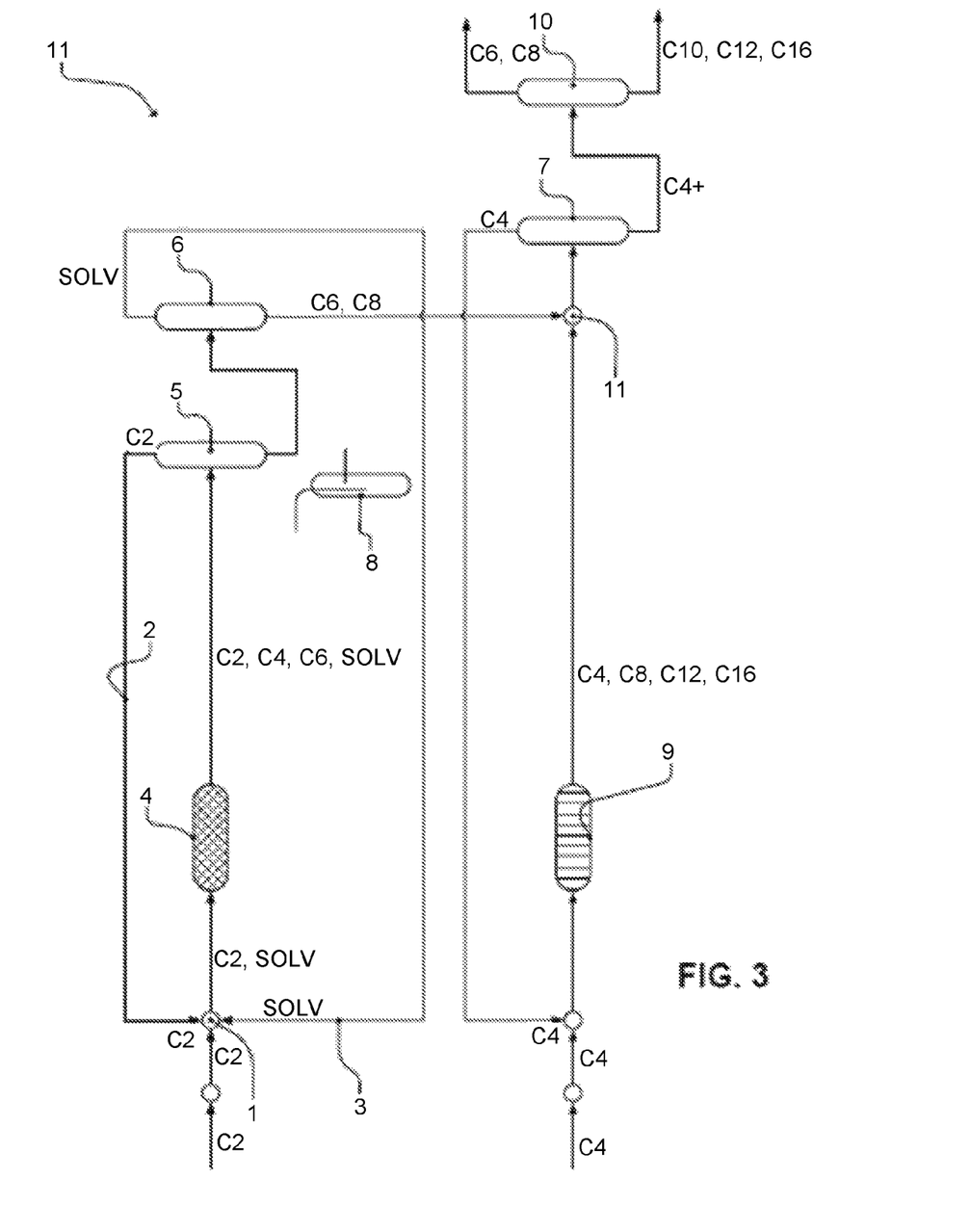
FIG. 3 shows a process flow diagram of a second embodiment II in oligomerization operation.
Figure 4:
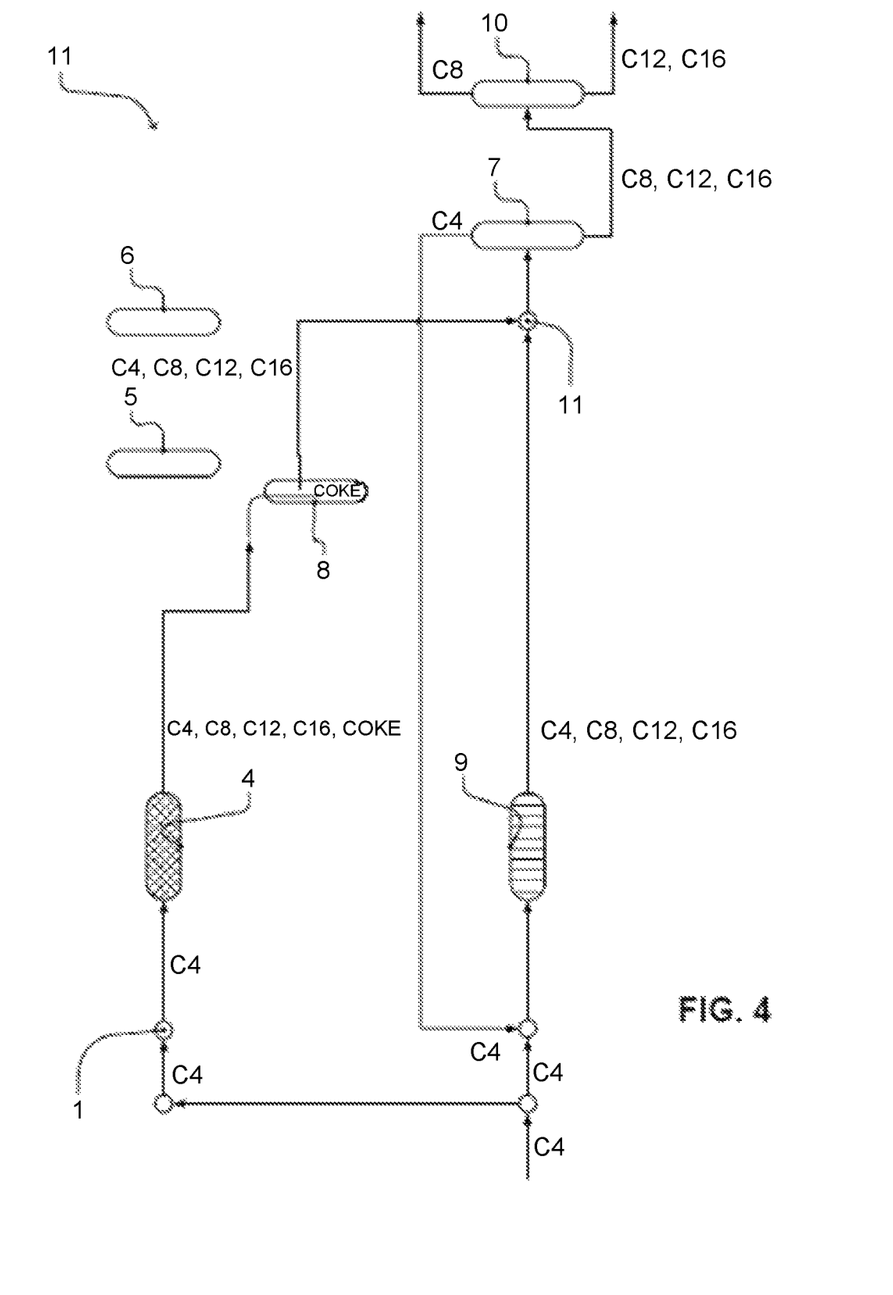
FIG. 4 shows a process flow diagram of the second embodiment II in regeneration operation.
Figure 5:
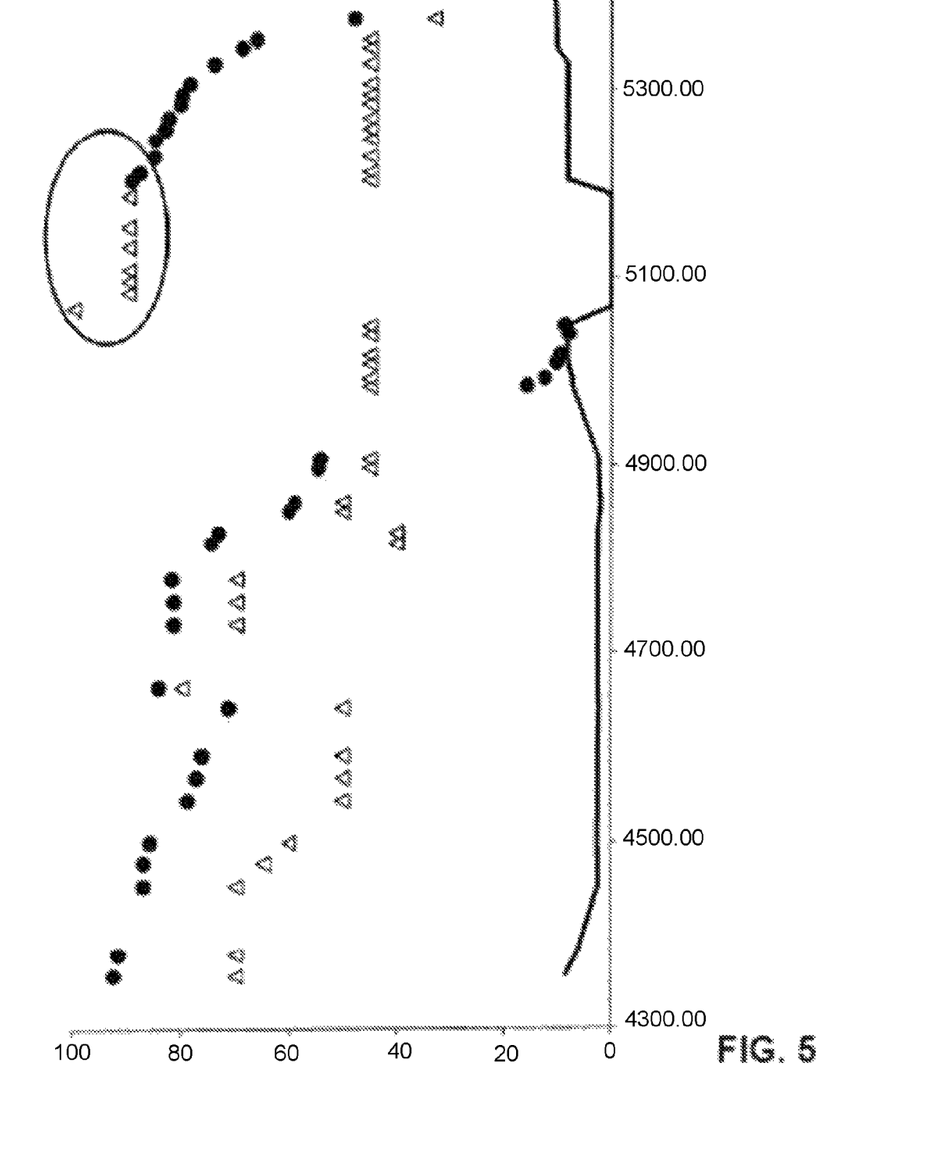
FIG. 5 shows reaction and regeneration phases in isobutane/raffinate III.
Figure 6:
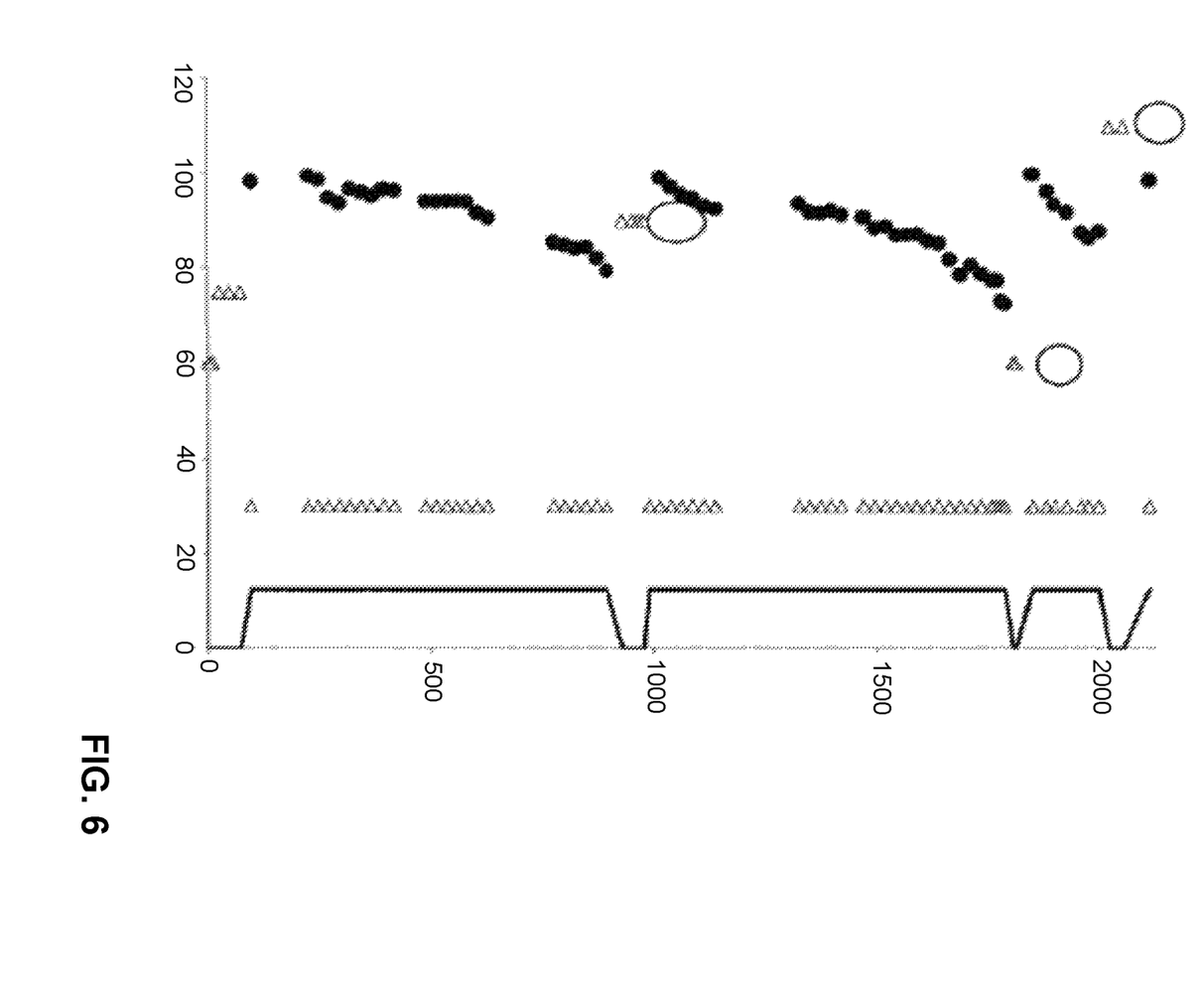
FIG. 6 shows reaction and regeneration phases in pure isobutane.
Figure 7:
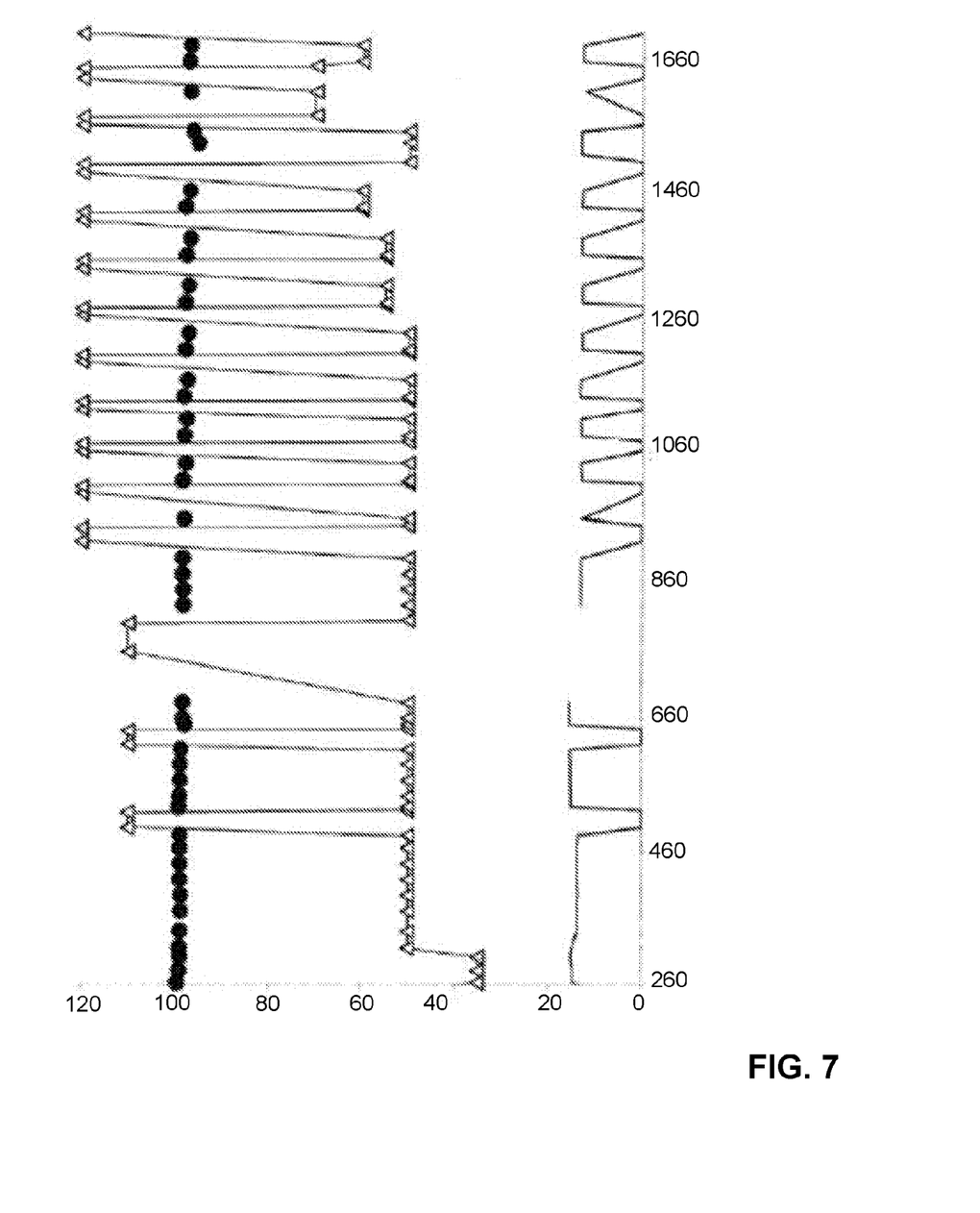
FIG. 7 shows reaction and regeneration phases in pulsed operation.

The industrial implementation of the invention is now to be elucidated by process flow diagrams and by experimental results. The figures show:

FIG. 1: Process flow diagram of a first embodiment I in oligomerization operation;

FIG. 2: Process flow diagram of the first embodiment I in regeneration operation;

FIG. 3: Process flow diagram of a second embodiment II in oligomerization operation;

FIG. 4: Process flow diagram of the second embodiment II in regeneration operation;

FIG. 5: Reaction and regeneration phases in isobutane/raffinate III (for example 1);

FIG. 6: Reaction and regeneration phases in pure isobutane (for example 2);

FIG. 7: Reaction and regeneration phases in pulsed operation (for example 3).

A process flow diagram for performance of a first embodiment I of the invention is shown in FIGS. 1 and 2, once in oligomerization operation and once in regeneration operation. This variant is characterized by the cycle mode of the solvent and the purge medium.

In oligomerization operation (FIG. 1), gaseous ethene C2 is mixed in a mixer 1 with a solvent SOLV to give a feed mixture C2, SOLV. The solvent is, for example, n-heptane, a $C_7$ alkane. The ethene is dissolved completely in the solvent, such that the feed mixture C2, SOLV is completely liquid and no bubbles of ethene gas form therein. Mixer 1 mixes fresh ethene from an ethene source (not shown) and recycled ethene from an ethene recycle line 2. The solvent SOLV comes from a solvent circuit 3.

The feed mixture C2, SOLV is run into a reactor 4 filled with a solid heterogeneous catalyst. The oligomerization of the ethene takes place in the reactor, over the catalyst, and within the solvent. This gives rise to a liquid oligomerizate C2, C4, C6, C8, SOLV, which comprises mainly the dimers of ethene $C_4$, trimers thereof $C_6$ and tetramers thereof $C_8$. In addition, the oligomerizate C2, C4, C6, C8, SOLV comprises unconverted ethene $C_2$ and unconverted solvent SOLV. The ethene C2 is unconverted since it was present in excess in the feed mixture and the residence time in reactor 4 was too short. The solvent is not converted since it is inert. Finally, the oligomerizate C2, C4, C6, C8, SOLV contains minimal amounts of higher oligomers and polymers having more than eight carbon atoms. However, this proportion is less than 5%.

The oligomerizate C2, C4, C6, C8, SOLV is then run into a first (distillation) column 5 and the excess ethene C2 present is removed overhead therein and recycled into the mixer 1 via the ethene recycle line 2. The excess ethene is thus not lost. What remain in the bottoms of the first column 5 are the olefins having more than three carbon atoms C2+ and the solvent SOLV.

In a second column 6, the bottoms from the first column are separated by distillation into a top product comprising the C4 and C6 olefins and a bottom product comprising the solvent and the C8 species.

The dimers C4 and trimers C6 are the actual products of value from the C2 oligomerization and are subjected to further workup (not shown).

In a third column 7, the solvent SOLV is removed by distillation overhead from the bottom product from the second column and introduced into the solvent circuit 3. The latter leads past a cold trap 8 back to the mixer 1.

What remain in the bottoms of the third column are the tetramers (C8) and small amounts of higher oligomers. As required, the bottom product from the third column 7 may be subjected to still further workup. The C8 olefins present therein are a possible third target product in addition to the dimers C4 and the trimers C6.

With time, the catalyst present in the reactor 4 is deactivated. In order to regenerate it, the ethene supply is shut down and the set temperature of the reactor 4 is increased. The solvent SOLV continues to be circulated via the solvent circuit 3, but now via the cold trap 8 and bypassing the columns 5, 6, 7. In this way, the plant assumes the regeneration operation shown in FIG. 2.

In regeneration operation, the n-heptane utilized as solvent SOLV now serves as purge medium. It detaches deposits COKE from the catalyst and carries them out of the reactor. The deposits COKE are frozen out of the purge medium SOLV in the cold trap 8 and remain in the cold trap 8. The purified purge medium SOLV is recycled to the reactor 4. On completion of regeneration, the system is switched back into the oligomerization operation shown in FIG. 1. The deposits COKE are removed from the cold trap.

A variant of the first embodiment I (not shown) could involve using a solvent SOLV with a different boiling point from n-heptane. The consequence of this would be that the column sequence has to be altered accordingly. If propane, for example, were to be used as solvent, it would have to be discharged overhead.

A further variant could involve not bypassing the cold trap 8 in oligomerization operation (cf. FIG. 1), and instead could involve the recycled solvent flowing through the cold trap even in oligomerization operation (solvent circuit 3 through the cold trap 8). This would have the advantage that any deposits already within the running production are removed from the solvent. The disadvantage is the loss of heat in the cold trap. The use of a non-thermal separation apparatus—for example a membrane—could provide a remedy in this respect. However, it is to be expected that far fewer deposits will be removed from the catalyst in the course of the oligomerization operation with the solvent than in regeneration operation, since the temperature is lower. In contrast to what is shown in FIGS. 1 and 2, the cold trap 8 may also be disposed directly beyond the reactor 4 in the downstream direction, in order to keep deposits away from the columns 5, 6 and 7 even in the course of oligomerization operation. However, this is associated with a thermal loss, and so the economic viability of this alternative arrangement of the cold trap should be examined carefully.

A second embodiment II of the invention is shown in FIGS. 3 and 4, again in oligomerization operation (FIG. 3) and in regeneration operation (FIG. 4).

The second embodiment II is to an extent identical to the first embodiment I, given that it also comprises a mixer 1 for provision of a feed mixture C2, SOLV, a reactor 4 for C2 oligomerization, a first column 5 for removal of the excess ethene C2, which is recycled via an ethene circuit 2, and a second column 6.

However, the solvent circuit 3 back to the mixer 1 already starts from the top of the second column 6, since the solvent SOLV used in this embodiment II is a mixture of isobutane and n-butene. The C4 substances are already distilled overhead in the second column 6. The higher oligomers C6, C8 from the bottoms from the second column are worked up in a second production chain, more of which later.

Since the solvent in the second embodiment II is a mixture of inert isobutane and reactive n-butene, a portion of the solvent is constantly being depleted by reaction in the reactor to give higher olefins (C8, C12, C16), which ultimately go into the second production chain.

At the same time, however, the dimerization of fresh ethene forms further n-butene in the reactor 4, and so the proportion of n-butene in the solvent can in principle, but need not, be kept constant. Thus, it is also possible to allow the n-butene content in the solvent to approach zero toward the end of an oligomerization phase.

The reason why n-butene is being used at least partly as solvent here is that, in this embodiment II, a C4 oligomerization is being conducted in a second reactor 9, in parallel to the C2 oligomerization. This C4 oligomerization converts n-butene C4 in the liquid phase over a solid heterogeneous catalyst which may but need not differ from the catalyst used in the C2 oligomerization.

The C4 oligomerization gives rise to a second oligomerizate C4, C8, C12, C16, which is worked up by distillation in a third column 7 and fourth column 10. The two columns 7 and 10 process the bottom product of the second column 6 as well. For this purpose, mixing is effected with the second oligomerizate in a second mixer 11.

In the regeneration operation of this embodiment II, the catalyst which is intended for the $C_2$ oligomerization and is present in the first reactor 4 is now contacted with the n-butene C4, which also serves as a feed mixture for the $C_4$ oligomerization in the second reactor 9 (FIG. 4). Thus, a reactive purge medium is used, which simultaneously purges the C2 catalyst, and the n-butene utilized as purge medium is also oligomerized over said catalyst. The heat of reaction which arises can be utilized in order to raise the set temperature for the first reactor 4 in regeneration operation. The combined regeneration and C4 oligomerization give rise to a third oligomerizate C4, C8, C12, C16, COKE in the first reactor 4, this being similar in terms of its components to the second oligomerizate C4, C8, C12, C16, but additionally containing the dissolved deposits COKE. Because of the similar composition, the spent purge medium (=third oligomerizate C4, C8, C12, C16, COKE) is run into the second mixer 11 via a cold trap 8 and mixed with the second oligomerizate C4, C8, C12, C16 therein, and they are worked up together by means of columns 7 and 10. The deposits COKE detached from the catalyst intended for the $C_2$ oligomerization are collected by the cold trap 8 and do not get into the second reactor 9.

On completion of the regeneration (FIG. 4), operation is switched back to oligomerization operation (FIG. 3). This still leaves a little n-butene C4 in the $C_2$ chain, which becomes part of the solvent SOLV therein.

Example 1: Oligomerization of Ethene to Isobutane and Regeneration of the Catalyst by Means of Hot Isobutane/Raffinate III Mixture 355 g of a heterogeneous catalyst based on nickel and silica-alumina (cf. U.S. Pat. No. 2,581,228) were introduced into an externally oil-heated and -cooled tubular reactor of length 2 m and internal diameter 2.1 cm, which had been provided with a thermocouple. Subsequently, mixtures of 2% to 10% by weight of ethene in isobutane were run over the catalyst in straight pass with total flow rates of 0.96 to 1.97 kg/h at set temperatures of 30 to 80° C. (WHSV=2.7 to 5.6 h$^{-1}$). The pressure was kept constant at 30*10$^5$ Pa. After a run time of 692 h, the ethene was shut down and replaced by a total flow rate of 1.38 kg/h of 80% by weight of raffinate III and 20% by weight of isobutane. The exact composition of this purge medium is shown in Table 1.

TABLE 1

| Purge medium composition | | | | | |
|---|---|---|---|---|---|
| 1-butene [% by wt.] | cis-2-butene [% by wt.] | trans-2-butene [% by wt.] | n-butane [% by wt.] | isobutane [% by wt.] | Other substances [% by wt.] |
| 26 to 29 | 11 to 12 | 20 to 22 | 17 | 22 | less than 0.5 |

This purge medium was used to "boil" the catalyst at an elevated temperature of briefly 100° C. and then 90° C. for 119 h (cf. FIG. 5, circled area). Subsequently, the system was switched back to 8% ethene in 1.18 kg/h of isobutane, which achieved a conversion of 89%. The exact operation intervals are apparent from FIG. 5. In this figure, the dot • represents the ethene conversion, the triangle Δ the set temperature (feed temperature of the oil) and the solid line—the proportion of ethene in the reaction mixture.

It was thus shown that, after a deactivation of the catalyst over a run time of 692 h, accompanied by a decrease in the ethylene conversion from 93% to 8% $C_4$ to $C_{16}$ oligomers, by boiling out the reactor with a mixture of isobutane and raffinate III at 90° C. for 119 h, it was possible to achieve a rise in the conversion back to 89% and hence the regeneration of the catalyst.

Example 2: Oligomerization of Ethene to Isobutane and Regeneration of the Catalyst by Means of Hot Isobutane 215 g of a heterogeneous catalyst based on nickel and silica-alumina (cf. U.S. Pat. No. 2,581,228) were introduced into an externally oil-heated and -cooled tubular reactor of length 2 m and internal diameter 2.1 cm, which had been provided with a thermocouple. Subsequently, a mixture averaging 15% by weight of ethene and 85% by weight of isobutane with a total flow rate of 1 kg/h was passed over said catalyst in straight pass at a set temperature of 30° C. (WHSV=4.7 $h^{-1}$). The pressure was kept constant at 30*$10^5$ Pa. At certain intervals, the ethene feed was stopped and the catalyst was "purged" at elevated temperatures with a flow rate of 1 kg/h of pure isobutane for different periods of time. It was possible here by the use of 20 μm filters (proceeding from a total amount of about 202 kg of ethene used) to isolate a total of 17 g of a white pulverulent substance, which was found to be polyethylene of low molecular weight distribution. The details relating to the reaction and regeneration phases are illustrated in FIG. 6. In FIG. 6, the dot • represents the ethene conversion, the triangle Δ the set temperature and the solid line—the proportion of ethene in the reaction mixture. The regenerations are circled. The data are compiled in Table 2.

TABLE 2

Regeneration protocol for Example 2

| Operation phases | Regeneration phases | Temperature | Duration [h] | Progress of deactivation (conversion loss) |
|---|---|---|---|---|
| 1st interval | 1st regeneration | 30° C. 90° C. | 840 h 48 h | 98% → 80% |
| 2nd interval | 2nd regeneration | 30° C. 110° C. | 624 h 6 h | 99% → 73% |
| 3rd interval | 3rd regeneration | 30° C. 110° C. | 168 h 32 h | 100% → 88% |

It is apparent from this that, with a run time of 840 hours, the ethylene conversion to $C_4$ to $C_{16}$ oligomers dropped from 98% to 80%. A first regeneration by means of isobutane at 90° C. for 48 hours raised the subsequent ethene conversion back to 99%. This dropped again from 99% to 73% during a further run time of 624 hours at 30° C. A second regeneration cycle by means of isobutane at 110° C. for 6 hours raised the subsequent ethene conversion to 100% again. After a further run time of 168 hours, the ethene conversion to $C_4$ to $C_{16}$ oligomers fell from 100% to 88% again. Regeneration by means of isobutane at 110° C. for 32 h enabled renewed ethene conversion of 99%.

Example 3: Pulsed Regeneration Operation

In a further experiment, 263 g of a heterogeneous catalyst based on nickel and silica-alumina were introduced into an externally oil-heated and -cooled tubular reactor of length 2 m and internal diameter 2.1 cm, which had been provided with a thermocouple. Subsequently, a mixture averaging 13% by weight of ethene and 87% by weight of isobutane with a total flow rate of 1 kg/h was passed over said catalyst in straight pass at a set temperature of 35° C. to 70° C. (WHSV=3.8 $h^{-1}$). The pressure was kept constant at 30*$10^5$ Pa.

At certain intervals, the ethene feed was stopped and the catalyst was "purged" at an elevated temperature of 110° C. to 120° C. with a flow rate of 0.87 kg/h of pure isobutane, with distinct shortening of the intervals for oligomerization operation and regeneration operation. The frequency of changeover arose from the monitoring of the ethene conversion (=(ethene used in the feed—unconsumed ethene in the output)/ethene used in the feed) in oligomerization operation: as soon as the continuously measured conversion of ethene in the oligomerization had dropped to 97%, a brief regeneration phase was inserted. After initial somewhat longer regeneration phases, it was found that an interval of 12 hours in each case appears to be sufficient under these reaction conditions, although these 12 hours are not an optimized value. In order, however, to be able to better interpret creeping changes, the regeneration time was kept constant for better comparability.

The operational changeovers are shown in FIG. 7. In this figure, the dot • again represents the ethene conversion, the triangle Δ the set temperature and the solid line—the proportion of ethene in the reaction mixture.

It is apparent that the oligomerization operation in this manner is frequently interrupted by a pulsed regeneration. At the same time, it becomes clear that the conversions can be kept at nearly 100% for longer in this way and that no noticeable irreversible losses of activity occur even in the long term. The use of 20 μm filters again made it possible (proceeding from a total amount of about 150 kg of ethene used) to isolate a total of about 2 g of a white pulverulent substance, which was found to be polyethylene of a low molecular weight distribution. From the distinctly smaller amount of polyethylene compared to the amount in Example 2, it can be expected that the catalyst will have a much longer life with the pulsed mode of operation.

CONCLUSION

The ethene conversion to $C_4$ to $C_{16}$ oligomers declines ever further in a linear manner with time without further intervention. If the catalyst were not to be regenerated again at certain intervals, the conversion would fall well below 80%. It has been shown that it is possible to reactivate the catalyst again without costly and inconvenient deinstallation of the catalyst, and instead merely by shutting down the ethene supply and purging with the hot solvent remaining. In this context, the elevated temperature of the solvent established homogeneously over the entire reactor is crucial for successful leaching-out of the poisoning component responsible for the deactivation. Pulsed regeneration operation enables better long-term stability of the catalyst.

KEY

I first embodiment
II second embodiment
1 mixer
2 ethene recycle line
3 solvent circuit
4 (first) reactor (C2-Oli)

5 first column
6 second column
7 third column
8 cold trap
9 second reactor (C4-Oli)
10 fourth column
11 second mixer
C2 ethene
C2, C4, C6, C8, SOLV oligomerizate (from C2-Oli in the first reactor)
C2, SOLV feed mixture
C2+ olefins having more than two carbon atoms
C4 dimers of ethene/n-butene
C4+ olefins having more than four carbon atoms
C4, C8, C12, C16 second oligomerizate (from C4-Oli in the second reactor)
C4, C8, C12, C16, COKE third oligomerizate (from C4-Oli in the first reactor)
C6 trimers of ethene
C8 tetramers of ethene/dimers of n-butene
C12 trimers of n-butene
C16 tetramers of n-butene
COKE deposits
SOLV solvent

The invention claimed is:

1. A process for oligomerizing ethene over a heterogeneous catalyst and for regenerating said catalyst, the process comprising the steps of:
   a) effecting the oligomerization in an oligomerization operation in which ethene, at least partly dissolved in a liquid solvent, is contacted with the heterogeneous catalyst;
   b) effecting the regeneration of the heterogeneous catalyst in a regeneration operation in which the heterogeneous catalyst in the absence of ethene, hydrogen and oxygen is purged with a liquid purge medium, wherein the heterogeneous catalyst is a solid containing at least two components, the first component containing at least one element selected from Ni, Cr, Fe, or Ti, and being in metallic and/or oxidic and/or hydridic form;
   c) alternating the oligomerization operation and regeneration operation over time, such that a time-limited oligomerization operation is followed by a time-limited regeneration operation, and the latter in turn by a time-limited oligomerization operation;
   d) locating the heterogeneous catalyst in one same location;
   e) supplying thermal energy to the location of the heterogeneous catalyst in order to impose a set temperature thereon; and
   f) setting the set temperature in the regeneration operation higher than the set temperature in the oligomerization operation.

2. The process according to claim 1, wherein both the liquid solvent and the liquid purge medium are selected from the alkenes having three to twelve carbon atoms or from the alkenes having three to ten carbon atoms or from mixtures thereof, this enumeration including the cycloalkenes.

3. The process according to claim 2, wherein the liquid solvent and the liquid purge medium are identical.

4. The process according to claim 3, wherein the liquid solvent and the liquid purge medium are one of the following substances or a mixture of two or more of these substances: propane, isobutane, pentane, cyclopentane, hexane, cyclohexane, heptane, cycloheptane.

5. The process according to claim 1 wherein the set temperature in oligomerization operation is between 20° C. and 130° C., and in that the set temperature in regeneration operation is between 80° C. and 1 50° C.; additionally with the proviso that the set temperature chosen in regeneration operation is higher than the set temperature in oligomerization operation.

6. The process according to claim 5, wherein the oligomerization operation is effected under the following conditions:
   Pressure: 0.1 MPa to 5 MPa
   WHSV: 2 $h^{-1}$ to 50 $h^{-1}$
   Ethene content in overall solution: 1% by weight to 50% by weight
and in that the regeneration operation is effected under the following conditions:
   Pressure: 0.1 MPa to 5 MPa
   WHSV: 2 $h^{-1}$ to 50 $h^{-1}$
   Ethene content in overall solution: 0% by weight to 1% by weight.

7. The process according to claim 1 wherein the duration of a regeneration operation is shorter than the duration of the preceding oligomerization operation, in that the duration of the regeneration operation is less than 20% of the duration of the preceding oligomerization operation.

8. The process according to claim 1 wherein the location of the heterogeneous catalyst where the regeneration operation and the oligomerization operation are effected is a reactor through which a temperature control medium flows for the purpose of supplying thermal energy, and in that the set temperature is set by the feed temperature of the temperature control medium.

9. The process according to claim 1 wherein the liquid purge medium is circulated in regeneration operation, and in that the liquid purge medium circulated, away from the location of the heterogeneous catalyst, is purified with the aid of a separation apparatus to free it of at least some components dissolved in the liquid purge medium.

10. The process according to claim 9, wherein the separation apparatus is a filter or a membrane or a cold trap, or a combination of two or more of these separation apparatuses.

11. The process according to claim 2, wherein the liquid purge medium is an alkene having three to twelve carbon atoms, or a mixture of two or more such alkenes, or a mixture of one or more such alkenes with at least one alkane having three to seven carbon atoms, wherein the liquid purge medium in regeneration operation is drawn off from the location of the catalyst and—optionally after purification—conducted to a second heterogeneous catalyst remote from the catalyst to be regenerated, and in that at least one alkene present in the liquid purge medium is subjected to a chemical reaction over the second catalyst, a second oligomerization, an isomerization or an etherification or an oxidative dehydrogenation.

12. The process according to claim 2, wherein the liquid purge medium is an alkane having three to seven carbon atoms or a mixture of two or more such alkanes, wherein the purge medium in regeneration operation is drawn off from the location of the heterogeneous catalyst and conducted to a second heterogeneous catalyst remote from the catalyst to be regenerated, and in that at least one alkane present in the purge medium is subjected to a chemical reaction over the second catalyst, a dehydrogenation to give alcohols and/or acid derivatives.

13. The process according to claim 1, wherein the second component comprises at least one metal oxide selected from $Al_2O_3$, $SiO_2$, $TiO_2$, or $ZrO_2$.

14. The process according to claim 1, wherein less than 5% by weight of the ethene converted in oligomerization operation is converted to oligomers or polymers of ethene having sixteen or more than sixteen carbon atoms.

15. The process according to claim 1, wherein the conversion of ethene is determined continuously in oligomerization operation, and in that there is then a changeover from oligomerization operation to regeneration operation when the conversion of ethene has dropped to a value between 95% and 100%.

16. The process according to claim 2 wherein the duration of a regeneration operation is shorter than the duration of the preceding oligomerization operation, in that the duration of the regeneration operation is less than 20% of the duration of the preceding oligomerization operation.

17. The process according to claim 2 wherein the location of the heterogeneous catalyst where the regeneration operation and the oligomerization operation are effected is a reactor through which a temperature control medium flows for the purpose of supplying thermal energy, and in that the set temperature is set by the feed temperature of the temperature control medium.

18. The process according to claim 2 wherein the liquid purge medium is circulated in regeneration operation, and in that the liquid purge medium circulated, away from the location of the heterogeneous catalyst, is purified with the aid of a separation apparatus to free it of at least some components dissolved in the liquid purge medium.

19. The process according to claim 3, wherein the liquid purge medium is an alkene having three to twelve carbon atoms or a mixture of two or more such alkenes or a mixture of one or more such alkenes with at least one alkane having three to seven carbon atoms, wherein the liquid purge medium in regeneration operation is drawn off from the location of the catalyst and—optionally after purification—conducted to a second heterogeneous catalyst remote from the catalyst to be regenerated, and in that at least one alkene present in the liquid purge medium is subjected to a chemical reaction over the second heterogeneous catalyst, a second oligomerization, an isomerization or an etherification or an oxidative dehydrogenation.

20. The process according to claim 3, wherein the liquid purge medium is an alkane having three to seven carbon atoms or a mixture of two or more such alkanes, wherein the purge medium in regeneration operation is drawn off from the location of the heterogeneous catalyst and conducted to a second heterogeneous catalyst remote from the catalyst to be regenerated, and in that at least one alkane present in the purge medium is subjected to a chemical reaction over the second catalyst, a dehydrogenation to give alcohols and/or acid derivatives.

* * * * *